United States Patent [19]

L'Esperance, Jr.

[11] Patent Number: 4,718,418
[45] Date of Patent: Jan. 12, 1988

[54] APPARATUS FOR OPHTHALMOLOGICAL SURGERY

[75] Inventor: Francis A. L'Esperance, Jr., Englewood, N.J.

[73] Assignee: LRI L.P., New York, N.Y.

[21] Appl. No.: 916,646

[22] Filed: Oct. 8, 1986

Related U.S. Application Data

[60] Continuation of Ser. No. 794,444, Nov. 4, 1985, abandoned, which is a division of Ser. No. 748,358, Jun. 24, 1985, abandoned, which is a continuation-in-part of Ser. No. 552,983, Nov. 17, 1983, abandoned.

[51] Int. Cl.$^4$ .......................... A61F 9/00; A61N 5/06; A61B 19/00
[52] U.S. Cl. ................................. 128/303.1; 128/395; 219/121 L; 219/121 LA; 219/121 LH; 219/121 LQ; 219/121 LR; 219/121 LW; 364/413
[58] Field of Search ............. 128/303.1, 362, 395–398; 219/121 L, 121 LA, 121 LG, 121 LP, 121 LQ, 121 LU, 121 LV, 121 LW

[56] References Cited

U.S. PATENT DOCUMENTS

| | | | |
|---|---|---|---|
| 3,465,091 | 9/1969 | Bradham, III et al. | 219/121 L |
| 3,769,963 | 11/1973 | Goldman et al. | 128/303.1 |
| 4,046,986 | 10/1980 | Kirkpatrick | 219/121 L |
| 4,173,980 | 11/1979 | Curtin | 128/303 R |
| 4,266,548 | 5/1981 | Davi | 128/303.1 |
| 4,316,074 | 2/1982 | Daly | 219/121 L |
| 4,504,726 | 3/1985 | Hosuka et al. | 219/121 LU |
| 4,564,737 | 1/1986 | Burke et al. | 219/121 LW |

FOREIGN PATENT DOCUMENTS

| | | | |
|---|---|---|---|
| 3148748 | 7/1983 | Fed. Rep. of Germany | 128/303.1 |
| 22982 | 2/1982 | Japan | 219/121 L |

OTHER PUBLICATIONS

"Microprocessor Controlled Laser Scanning System for Annealing of Semiconductors", Heidary et al.; Optics & Laser Tech., 10/81.
"Two Pass Laser Cutting", by Shah et al.; IBM Tech. Disclosure Bul., vol. 16, #10, 3/74.
"The Changing Status of Radical Keratotomy for Myopia, Part II", by Waring, M. D., Jour. of Refractive Surgery, Jul./Aug. 1985, vol. 1, #3.

*Primary Examiner*—Lee S. Cohen
*Assistant Examiner*—David Shay
*Attorney, Agent, or Firm*—Hopgood, Calimafde, Kalil, Blaustein & Judlowe

[57] ABSTRACT

The invention contemplates use of a scanning laser characterized by ultraviolet radiation to achieve controlled ablative photodecomposition of one or more selected regions of a cornea. Irradiated flux density and exposure time are so controlled as to achieve desired depth of the ablation, which is a local sculpturing step, and the scanning action is coordinated to achieve desired ultimate surface change in the cornea. The scanning may be so controlled as to change the front surface of the cornea from a greater to a lesser spherical curvature, or from a lesser to a greater spherical curvature, thus effecting reduction in a myopic or in a hyperopic condition, without resort to a contact or other corrective auxiliary lens technique, in that the cornea becomes the corrective lens. The scanning may also be so controlled as to reduce astigmatism and to perform the precise incisions of a keratotomy. Still further, the scanning may be so controlled as to excise corneal tissue uniformly over a precisely controlled area of the cornea for precision accommodation of a corneal transplant.

41 Claims, 16 Drawing Figures

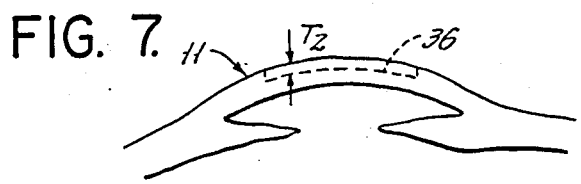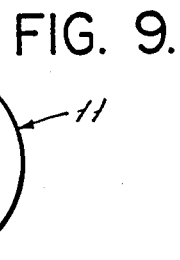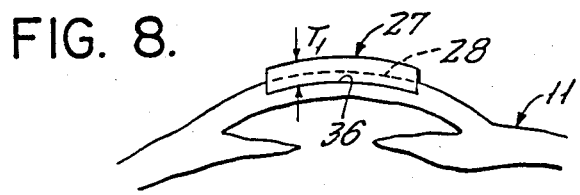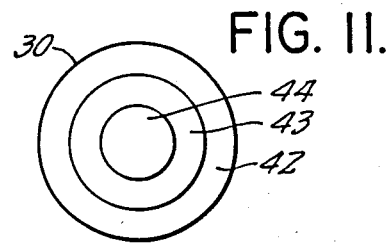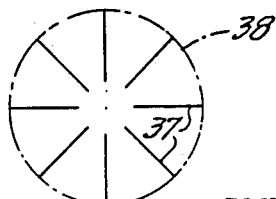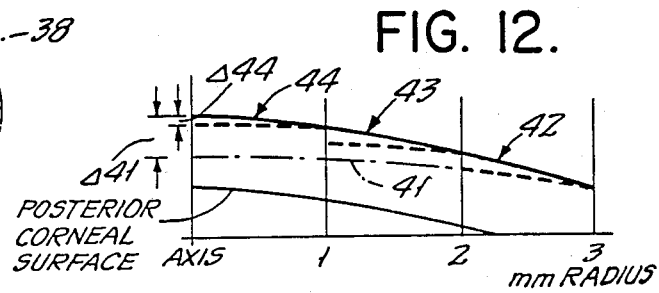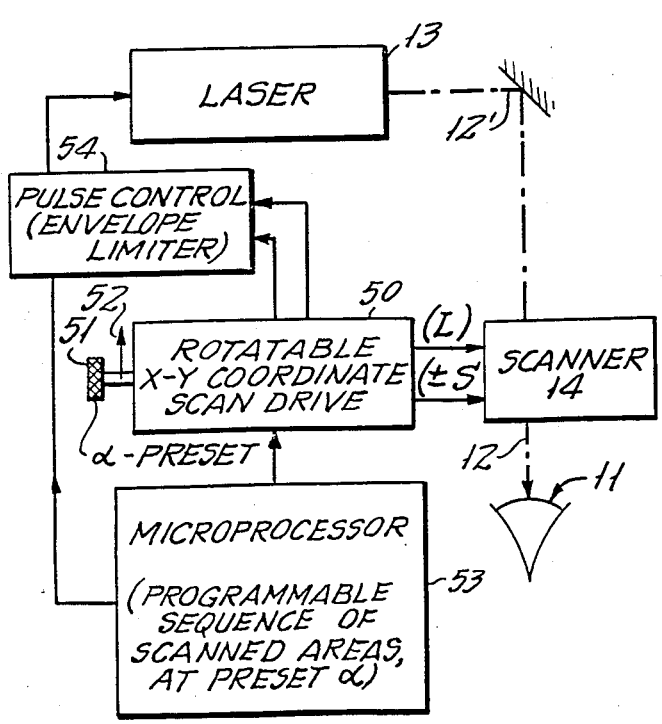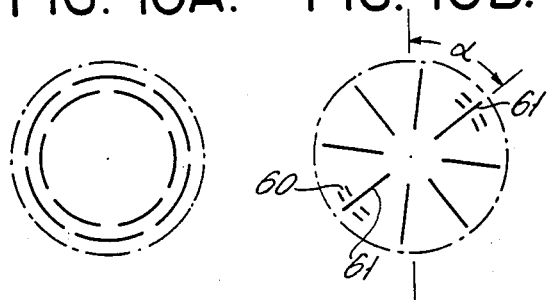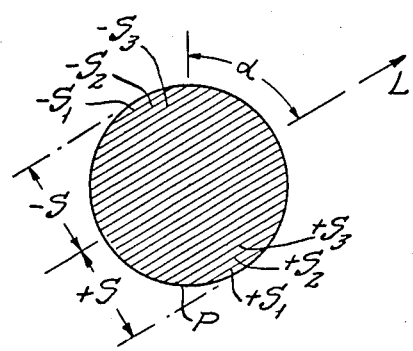

APPARATUS FOR OPHTHALMOLOGICAL SURGERY

RELATED CASE

This application is a continuation of pending divisional application Ser. No. 794,444, filed Nov. 4, 1985, now abandoned which was a division of Ser. No. 748,358, filed June 24, 1985, now abandoned which was a continuation-in-part of application Ser. No. 552,983, filed Nov. 17, 1983, now abandoned.

BACKGROUND OF THE INVENTION

The invention relates to that aspect of ophthalmological surgery which is concerned with operations upon the external surface of the cornea.

Operations of the character indicated include corneal transplants and keratotomies; such operations have traditionally required skilled manipulation of a cutting instrument. But, however keen the cutting edge, the mere entry of the edge into the surface of the cornea necessarily means a wedge-like lateral pressure against body cells displaced by the entry, on both sides of the entry. Such lateral pressure is damaging to several layers of cells on both sides of the entry, to the extent impairing the ability of the wound to heal, and resulting in the formation of scar tissue.

The $CO_2$ laser has been employed in an effort to minimize such surgical damage to cells on severed sides of a given cut, as in the case of operations to remove a local skin defect. The beam of such a laser is characterized by a particular infrared wavelength (10.6 microns), and controlled local ablation or incision of the cornea is achieved, without developing any lateral pressure upon cells adjacent to the margins of ablation. However, the operation is not performed without side effects, in that the ablation or incision is thermally achieved, through photocoagulation and/or photovaporization; cells adjacent the ablated or incised margin are charred. And even with lasers emitting in the visible spectrum, the effect is still largely thermal in nature. For example, for visible laser irradiation of the skin at about 532.0 nanometers (0.532 micron), namely, in the pea-green portion of the visible spectrum, histological examination reveals evidence of cellular dehydration (i.e., cellular retraction with formation of tissue clefts, pyknotic nuclei) at energy densities where ablation can be accomplished; thus, at an energy level needed for ablation or incision with such radiation, charring (cellular damage) is observed at the site of the incision and is an indication of substrate heating.

On the other hand, radiation at ultraviolet wavelengths is characterized by high photon energy, and this energy is greatly effective on impact with tissue, in that molecules of tissue are decomposed on photon impact, resulting in tissue ablation by photodecomposition. Molecules at the irradiated surface are broken into smaller volatile fragments without heating the remaining substrate; the mechanism of the ablation is photochemical, i.e., the direct breaking of intra-molecular bonds. Photothermal and/or photocoagulation effects are neither characteristic nor observable in ablations at ultraviolet wavelengths, and cell damage adjacent the photodecomposed ablation is insignificant.

BRIEF STATEMENT OF THE INVENTION

It is an object of the invention to provide an improved apparatus and technique for surgically operating upon the outer surface of the cornea.

Another object of the invention is to provide apparatus and technique for surgically modifying optical properties of the eye through surgical procedure on the outer surface of the cornea.

It is a specific object to provide surgical techniques and apparatus for reducing a myopic, for reducing a hyperopic, and/or for reducing an astigmatic condition of an eye.

Another specific object is to provide an improved surgical technique in performing corneal-transplant operations.

A still further specific object is to provide automatic means for safely applying ultraviolet irradiation in surgical procedures on the cornea.

The invention achieves these objects with apparatus which effectively fixes the position of an eye with respect to a scanning laser characterized by ultraviolet radiation, at an energy level capable of achieving controlled ablative photodecomposition of the cornea, namely, of the epithelium, Bowman's membrane, and stroma levels of the cornea. Irradiated flux density and exposure time are so controlled as to achieve desired depth of the ablation, which is a local sculpturing step, and the scanning action is coordinated to achieve desired ultimate surface change in the cornea. The scanning may be so controlled as to change the front surface of the cornea from a greater to a lesser spherical curvature, or from a lesser to a greater spherical curvature, thus effecting reduction in a myopic or in a hyperopic condition, without resort to a contact or other corrective auxiliary lens technique, in that the cornea becomes the corrective lens. The scanning may also be so controlled as to reduce astigmatism, and to perform the precise incisions of a radial or other keratotomy. Still further, the scanning may be so controlled as to excise corneal tissue uniformly over a precisely controlled area of the cornea for precision accommodation of a corneal transplant.

DETAILED DESCRIPTION

The invention will be illustratively described in detail, in conjunction with the accompanying drawings, in which:

FIGS. 7 and 8 are views in section, and FIG. 1 is a view in front elevation, to illustrate use of the invention in a corneal transplant operation;

FIG. 9 is a view in front elevation to illustrate preparation of a recipient cornea for a corneal transplant;

FIGS. 10, 10A and 10B are views in front elevation to illustrate use of the invention in different keratotomy operations;

FIGS. 11 and 12 are, respectively, a view in front elevation and an enlarged half-section-profile diagram to illustrate a Fresnel-cut use of the invention;

FIG. 13 is a schematic diagram to illustrate apparatus modified to perform an astigmatism-correcting operation; and FIG. 14 is a view similar to FIGS. 3 and 4, to illustrate an astigmatism-correcting operation with the apparatus of FIG. 13.

Figure 1:
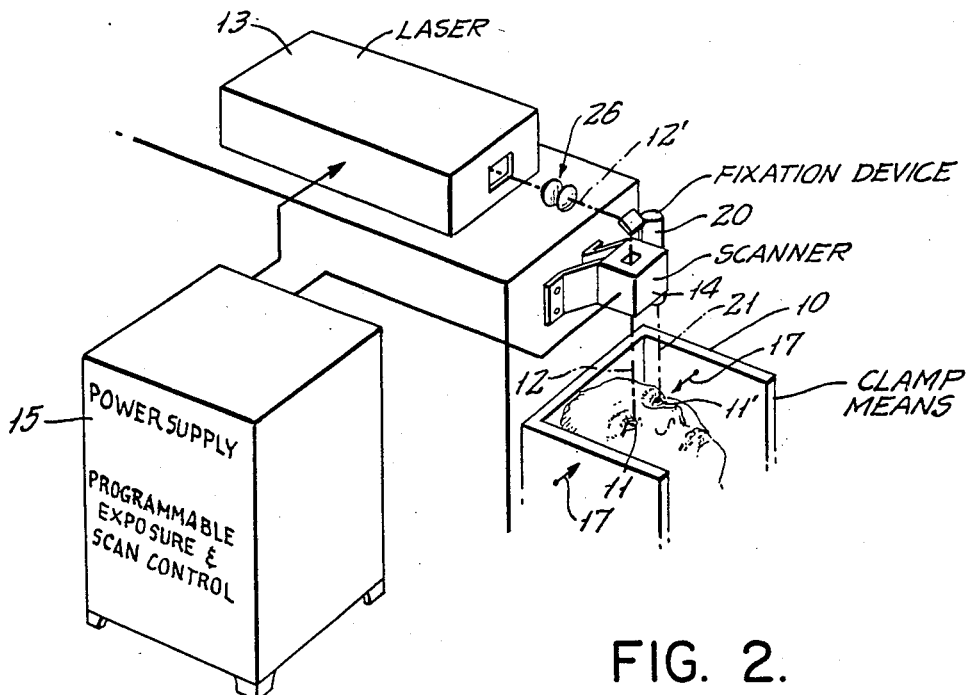
FIG. 1 is a schematic diagram in perspective, to show the general arrangement of operative components of the invention.

In FIG. 1, clamp means 10 is shown for fixed retention of the head of a patient (reclined, face up) such that the eye 11 to be operated upon is fixedly aligned with a downwardly folded portion 12 of the central axis 12' of beam output from a stationary laser device 13, and scanner means 14 is provided for programmed deflection of laser-beam output, with respect to the central axis 12. The laser device 13 is served by a suitable power supply 15, and the scanner means 14 includes selectively operable control means, suggested by legend, for determining scan pattern, effective limits of scan action, and, if desired, the time-varying profile of one or more dimensional components of scan action.

Preferably, the clamp means 10 includes means, symbolized at 17, to stabilize the patient's head via opposed engagements at the region of his temples, and an eye-retaining fixture (18, FIG. 3) peripherally engages eye 11 at the corneal-scleral area. Also preferably, an optical-fixation device 20 is adjustably fixed, as to the housing of scanner 14. Illustratively, device 20 includes a sighting reticle and lens, whereby the eye 11' not being operated upon can view the reticle as if at infinity; the sighting alignment 21 for device 20 is parallel to the axis 12, and it will be understood that adjustable means (not shown) may provide an adjustable offset, as needed for accommodation of the patient's interpupilary distance and to adapt to the particular mounted offset of device 20 from axis 12. For an operation on the other eyed 11', the eye 11 will be available for similar fixation, in conjunction with another fixation device (not shown) and associated adjustably offsetting means; alternatively, the fixation device 20 may be adjustably mounted at correct offset on the opposite side of scanner 14. For purposes of operating on eye 11', clamp means 10 will have been indexed laterally with respect to laser 13 to the extent aligning axis 12 with the eye (11') then to be operated upon, thereby positioning eye 11 for use of the fixation device.

Figure 2:
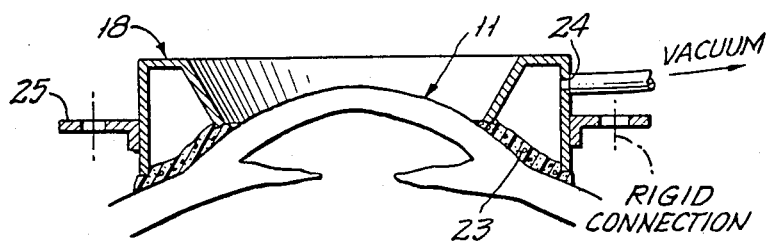
FIG. 2 is a simplified view in longitudinal section, showing an eye-retaining fixture used with the apparatus of FIG. 1.

The eye-retaining fixture 18 of FIG. 2 is seen to comprise a hollow annulus, having a convergent axial-end wall 23 of air-permeable material contoured to engage and retain the eye via a scleral-corneal region. A sideport connection 24 to a vacuum pump enables retention of eye engagement to wall 23, and outward lug or flange means 25 enables rigid aligned and spaced connection of fixture 18 to laser 13 and its scanner 14 via means suggested by legend in FIG. 2, such means being omitted from FIG. 1 for reasons of more simplified showing.

The laser selected for use at 13 preferably emits in the ultraviolet, namely, at wavelengths of less than substantially 400 nanometers. Such emissions for gas lasers are characteristically at 351 nm for xenon-fluoride lasers, 337 nm for nitrogen lasers, 308 nm for xenon-chloride lasers, 248 nm for krypton-fluoride lasers, 193 nm for argon fluoride lasers, and 157 nm for fluorine lasers; and within this range, frequency-doubling techniques applied to other lasers, including crystal lasers, provide further alternative sources.

One of the existing commercial excimer-laser products of Lambda Physik GmbH, Gottingen, Germany, for example their Model EMG 103 operating with argon-fluoride, is satisfactory for use as laser 13; for this product, maximum energy per pulse is 200 millijoules, with a pulse-repetition rate of 200 per second, $3 \times 10^5$ shots being available from a single charge of the involved gas, before reducing to 50 percent of specified power at this repetition rate, it being noted that full rated power is not necessarily required in use of the present invention. Pulse width is about 15 nanoseconds, and typical beam dimensions at 25 centimeters (10 inches) are 10 mm $\times$ 22 mm. To bring this down to an illustratively useful rounded-square spot size of 0.5 mm by 0.5 mm at the eye 11, corrective lens elements at 26, as of quartz, calcium fluoride, or magnesium fluoride, will be understood to include a cylindrical element and a spherical element whereby beam size is reduced while the rectangular section is compressed to substantially square section.

Figure 3:
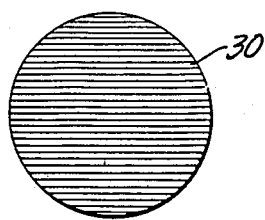
FIGS. 3 and 4 are simplified diagrams to illustrate different scan patterns performed with apparatus as in FIG. 1.
Figure 4:
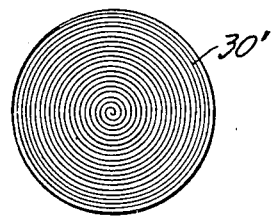

FIGS. 3 and 4 illustrate alternative scan patterns for having the typical half-millimeter focused and repetitively pulsed spot of the laser beam course the surface of eye 11 in the performance of a surgical procedure. The circle 30 in FIG. 3 may illustratively be of 6-mm diameter at the cornea, and centered on the axis of eye 11. The scan action is rectilineal, involving plural horizontal line scans with progressive vertical displacement to cover the field, here shown limited to the circle 30. For this purpose, a suitable scanner, known as "Microscan 771", is commercially available from Laser Industries, International, Hendon, England and therefore need not be here described in detail. It suffices to say that the control means 16 associated with such a scanner includes a microprocessor with memory for delineated boundary limits of scan, such as the limiting circle 30. The delineation can be to the surgeon's desired boundary contours, and the scan speed and direction may be programmed or manually controlled. What has been said as to FIG. 3 also applies to FIG. 4, except that a spiral course of scan, i.e., rotary sweeps at progressively changing radius, is involved in each coverage of the delineated field 30'.

It is a feature of the invention that the programming of scan action be such that predetermined depth of ultraviolet laser incision be made to effectively re-characterize the external contour of the cornea within the entire predetermined field boundary (e.g., 30, 30'). This is done by progressive precise photodecomposition of the corneal tissue, as to a depth limit of 0.35 mm. In the illustrative argon-fluoride laser referenced above, a precise volume of tissue (e.g., 14 microns deep) may be excised for each laser pulse or shot, and the half-millimeter spot, repeated at 200/second, can cover the entire area within the delineated boundary 30, in about fifteen seconds.

Figure 5:
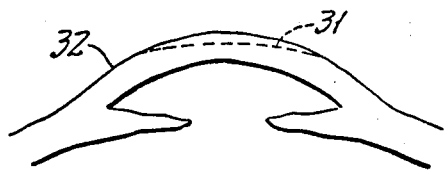
FIGS. 5 and 6 are simplified sectional views to illustrate different sculptured surface curvatures achieved with either of the scan patterns of FIGS. 3 and 4.

For the situation depicted in FIG. 5, the dashed line 31 represents the ultimate curvature to which the external surface of a cornea 32 may be modified to achieve a change in optical properties of the involved eye, here illustratively a myopic eye, for which the reduced curvature 31 offers a diopter-reducing corrective effect, all without resort to the use of a spectacle lens or a contact lens to achieve the result. To achieve the curve 31, the minimum desired photodecomposition is at the outer boundary 30, and the maximum is at the center. This is achievable by programming the microprocessor to progressively reduce the radius of the boundary circle 30

(i.e., progressively reduce the area of scanned field), for successive scans of the reducing field. If the curvature 31 requires a maximum depth of 0.35 mm of cornea removal at the center, this means that the central region of the cornea (i.e., the last and most reduced scanned field) will have been scanned twenty-five times, and that cornea removal outside this most reduced scanned field will have involved lesser numbers of scans, the progression having been predetermined to achieve the desired ultimate curvature 30 over the area 31.

What has been said as to the scan technique of FIG. 3 to achieve curvature 31 applies equally for use of the spiral scan of FIG. 4, the field 30' again being programmed for automatic reduction as necessary to provide maximum cornea removal at the center, and minimum at outer limits of the circular boundary.

Figure 6:
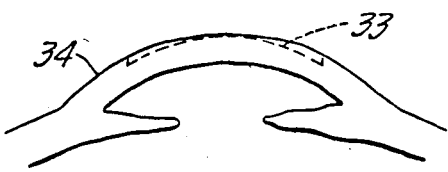

What has been said as to programming to achieve lesser curvature in the outer surface of the cornea (FIG. 5), to reduce a myopic condition, applies also to FIG. 6 for reduction of a hyperopic condition. In FIG. 6, the difference lies in programming field scans so as to initiate and progressively enlarge a central area which defines the inner limit of field scanned. Thus, except for perhaps one field scan involving cornea removal over the entire area bounded by circle 30 (30'), all remaining field-scanned areas are annular, with progressively increasing inner radius of each successively scanned annular field. The last such "field" will necessarily be virtually a circular line at the diameter of circle 30 (30'), along which circular line the depth of surgical excision will have been greatest, as indicated by dashed line 33 in the cornea 34 of FIG. 6.

Quite aside from the variable-depth character of the removal of corneal tissue (FIGS. 5 and 6), the invention also lends itself to uniform-depth removals, over the entire area of a multiply-scanned constant field. In FIGS. 7 and 9, the cornea of an eye 11 is subjected to a succession of scans of (i.e., within) a constant predetermined field area 35. In the illustrative laser case, with excision to a depth of 14 microns for each pulse, a uniform depth of 0.35 mm is achieved by 25 scans of the total area 34, to produce a carved base or floor curvature 36 for reception and location of a corneal transplant.

Further with respect to a corneal-transplant procedure, the described apparatus will be seen to be further useful, as in preparation of the corneal insert to be implanted at and within the recess 36. A donated eye may be reversibly held to a fixture as described at 18 in FIG. 2; by "reversible" it is meant that, depending upon the manner of mounting flange 25, either the epithelium or the endothelium of the donated eye may be mounted for upward exposure to the laser beam 12, it being understood that for the latter situation with the donated eye, iris and other regions not needed for corneal-scleral mounting and for corneal operation will have been initially removed. A preferred procedure is first to so expose to laser scanning the concave inner side of the donated cornea; such scanning is to an extent (achieved by multiple scans of a full circular field exceeding the diameter of recess 36) sufficient to remove tissue at least to a uniform depth within the stroma, whereupon the mounting of fixture 18 (and its partially machined corneal workpiece) is reversed, to expose to laser scanning the convex outer side of the donated cornea. Scanning the outer side consists of two steps: first, multiple scans of the full circular field (exceeding the diameter of recess 36), thereby excising at least the epithelium and to a depth which preferably achieves a transplant thickness $T_1$ exceeding the depth $T_2$ of recess 36; second, scanner 14 is operated in a line-cutting mode wherein successive laser pulses sequentially advance along the circumference of a circle designed for precise acceptance in the circular recess 36, until full severance of the circular cut-out, which then becomes the prepared transplant. Upon implanting, donated stroma is placed in full endothelium-free contact with the patient's prepared stroma, and the implant may be sutured. Later, upon removal of sutures, the outer surface of the eye 11 and its transplant 27 will have the appearance shown in FIG. 8, wherein the transplant projects beyond adjacent areas of the patient's cornea, and this projecting surface of the transplant may be reduced by laser scanning to a finish contour 28 of preferably flush marginal conformance with non-sculptured adjacent tissue of the patient's eye. It will be further understood that, subject to the surgeon's decision, such a finishing cut may be to a curvature which does or does not effect a predetermined change in optical performance of the eye.

FIG. 10 illustrates a modified use of the described apparatus, as for developing the plural angularly spaced radial cuts 37 involved in a radial keratotomy, all within a predefined circular limit 38. Depending upon the severity of the condition which calls for a keratotomy procedure, the depth of radial cuts 37 may exceed the 0.35 mm depth illustratively given for FIGS. 5 to 8.

Certain myopic and hyperopic conditions may be so severe that to produce merely an excised single surface 31 or 33 could involve, in the surgeon's considered judgment, an excessive removal of tissue, at the involved region of necessarily deepest cut. For such a situation, the invention offers the option of programming successive scans in a manner to create a Fresnel-type stepped development of the desired ultimate curvature. Such a situation and procedure are illustrated in FIGS. 11 and 12, wherein an ultimately reduced-curvature surface 31 of FIG. 5 (dashed line 41 in FIG. 12) is achieved in annular increments within the field area bounded at 30. In the outer one of these annuli (42), the curvature and depth of cut are precisely as would have applied to generate the continuous curve 41 (i.e., without Fresnel steps). But the intermediate annular area 43 effectively achieves a continuation of curve 41 with much less volume of corneal excision. Finally, the inner circular area 44 effectively completes curve 41, with minimal removal of corneal tissue.

The removal of tissue at the center is denoted $\Delta_{44}$ for the Fresnel cut 44 of FIGS. 11 and 12 and comparatively, is but a small fraction of the maximum removal depth $\Delta_{41}$ which would be needed to achieve the same optical correction with the smoothly developed corrected single-curvature surface 41. It will be understood that for the Fresnel-type cut as illustrated in FIG. 12, the previously described illustrative half-millimeter spot size will be incapable of achieving the desired result, for the one-millimeter radial increments shown in FIG. 12. To produce the requisite resolution for characterizing increments of curvature 41 at 42, 43, 44, it is necessary to employ a smaller spot size. For the indicated Lambda Physik equipment, spot-size reduction is feasible via means 26 as far as to produce a 30-micron spot size, if necessary; with this capability, it is seen that the one-millimeter radius increments of annulus 42 and annulus 43 are each achievable with a resolution of about 35 radial steps per increment (42 or 43). It will thus be understood that numbers given above are for purposes of more simplified illustration of this and the other aspects of the present invention.

In the discussion thus far, an excimer laser has been the illustrative source of an ablating beam, and it has been generally indicated that other lasers are available as alternative sources in the desired ultraviolet region and at presently suitable energy levels, and these other lasers will emit continuously for periods of controlled duration. For example, an organic-dye laser utilizing the proper organic dye can be made to produce laser emission in the region of 380 nm when pumped by an ultraviolet laser source such as a continuous-wave neodymium-YAG laser operating at 266 nm; in this case, the organic-dye laser emission at 380 nm can be frequency-doubled by a proper non-linear crystal such as a potassium-titanium-phosphate (KTP) crystal to an emission wavelength of 190 nm.

The showing of FIGS. 1 to 5 will thus be understood to illustrate the further case wherein ultraviolet laser radiation on axis 12 is of continuous-wave nature, for programmed exposure and scan control at 15, such that the per-unit time exposure of a given element of scanned area on a given scan-deflected pass of the elemental area involves beam-exposure flux at a level at which resultant corneal-tissue ablation per scan is to an ascertained elemental depth which is but a fraction of desired maximum ablation into the stroma region of the cornea. The desired maximum ablation therefore results from programmed exposure to successive continuous-wave scans of the local area requiring deepest incision, to effect the desired corrected anterior-surface profile of the cornea. And it will be understood that continuous-wave scanning is also equally applicable to the various sculpting purposes and techniques described in connection with FIGS. 7 to 12.

FIGS. 13 and 14 illustrate applicability of the invention to the correction of an astigmatism which has been identified in a particular eye. In this situation, the anterior surface of the untreated eye exhibits a cylindrical component of curvature which is a departure from otherwise generally spherical curvature, and the orientation of the axis of cylindrical curvature is at a particular angular orientation $\alpha$ with respect to the central vertical axis of the eye. FIG. 14 indicates this angle $\alpha$ in the context of a circular area of perimeter P to be subjected to astigmatism-correcting laser-scanning ablation. For the depicted illustrative case, area scanning of progessively changed areas utilizes a rectilinear X-Y coordinate drive 50 of scanner 14, wherein the orientation of the X-Y coordinate system can be angularly adjusted by selectively operable means symbolized by a knob 51 having associated means 52 to indicate the angle-$\alpha$ setting appropriate to the eye 11 requiring correction. The X-Y coordinate scan drive 50 is shown under control of microprocessor means 53, with indication that means 53 is programmable to govern a sequence of scanned areas, at the preset angle $\alpha$.

For discussion purposes, it is indicated in FIG. 14 that adjusted angular displacement of the X-Y components of scan action establishes the line-scan orientation L for the line-scan component and the transverse offset S for the line-displacement component of rectilinear scan, plus and minus directions being shown for the transverse offset S, with respect to a central alignment of symmetry in the L direction. Pulse-control or gating means 54 is shown with input connections from the scan-drive means 50 and from microprocessor means 53, and with an output connection 55 to determine gated on/off control of laser output in the course of area scanning.

More specifically, and assuming the case of progressive reduction of scanned areas to reduce the astigmatism, a first area scan may be effected by a succession of parallel L-oriented sweeps, at incremental advance of transverse offset S, commencing with a first short chordal sweep $-S_1$, and progressing across almost the full circular area (within perimeter P) until termination of the first area scan at the symmetrically opposite short chordal sweep $+S_1$, thereby ablating a first slightly truncated area (within perimeter P) to a first incremental depth in the cornea. On the next area coverage, the limiting outer parallel truncations $-S_2$ and $+S_2$ apply, to create a second area of incremental ablating intrusion which symmetrically laps (and is therefore cumulative with) all but the outer increment of truncations, from $-S_1$ to $-S_2$, and from $+S_1$ to $+S_2$. In like fashion, successive area scans are at progressively shrinking spans between symmetrically inwardly displaced parallel truncations, $-S_3$ ($+S_3$), and so on, until the final area scan is of line or virtually line thickness, namely, when scanning the laser beam essentially only on the central axis of symmetry, on axis L. The net result of cumulative ablation is to achieve desired maximum depth of sculptured cut on the central axis of symmetry, at the preset orientation $\alpha$, with depth of cut which gradually reduces to a minimum at the outer truncation lines $-S_1$ ($+S_1$). It will be understood that the sculptured profile of cut may be cylindrical, to the extent of effecting a prescribed number of diopters of cylindrical correction, depending upon the programming of scan-area reduction predetermined at 53. And it will be further understood that the same kind of cumulative ablative scupture to achieve a cylindrical-surface correction can be obtained for a program of successive-area scanning wherein the first-scanned area is narrow and on the central axis (L) of symmetry, with area-expansion between widening limits of the parallel truncations, to the point of finally scanning at the shortest and outermost truncations $-S_1$ and $+S_1$ of the area described by perimeter P.

In use of the invention for laser surgery upon an eye having need for both astigmatic and spherical correction, it is preferred that the astigmatic correction, described in connection with FIGS. 13 and 14, be the first of two procedures. This is considered advantageous because astigmatic errors are generally not as severe as spherical errors, so that fewer diopters of cylindrical-curvature ablation will be involved than for the subsequent spherical-correction procedure. Furthermore, to have eliminated or substantially eliminated the astigmatism in a first procedure is to have constituted the anterior surface of the cornea to an essentially spherical surface, which (be it myopic or hyperopic in nature) is more assuredly correctively sculpted to the desired profile (also spherical) for emmetropia vision, particularly where, as is the case of this invention, all ablative-laser area scans are effectively centered on the optical axis of the eye.

It will be seen that the described methods and apparatus achieve all stated objects and provide readily controlled procedure for correcting eye abnormalities attributable to cornea curvature. The ablative penetration of laser beam action may be kept to a relatively harmless fraction of the thickness of the cornea, and whatever the depth of invasion, a natural body process provides protective epithelium coverage of the sculpted region, within a few days after an operation. The programmable coordination of scan-area size and shape (circular, annular, or truncated) in conjunction with unit-time exposure at given sizes and shapes will produce predictable and controlled changes in curvature, whereby cylindrical errors and/or spherical errors may be eliminated or substantially reduced, to the enhanced comfort and convenience of the patient.

While the invention has been descrbed in detail for various illustrative embodiments and modes, it will be understood that modifications may be made without departing from the scope of the invention. For example, what has been described above as manual means 51 to preset the angle at which astigmatic correction is to be achieved, may in fact be an automatically driven setting of the astigmatic-correction angle, wherein the angle-input data for making the automatic drive is produced by a diagnostic system or method as descibed in my copending patent application, Ser. No. 691,923, filed Jan. 16, 1985.

Also, it will be understood that, although preferred, it is not necessary to limit area-scanning to the circular perimeter P when sculpting for astigmatism correction. The circle perimeter P represents a preferred minimum area of ablative sculpture, being that maximum circular area involved for sight under dilated-pupil conditions, e.g., about 7-mm diameter. However, the corneal-area outside this perimeter P is not required for best central sight and therefore no opticall-related harm results if the scanning procedure is such as to ablate in regions outside perimeter P. Thus, in FIG. 13, it is not strictly necessary that pulse-control means 54 shall have the "envelope limiter" (i.e., perimeter P limiting) function suggested by legend. In other words, a purely rectangular accomplishment of all area scans, from a "single-line" area on the axis (L) of symmetry to outer limits $-S_1$ and $+S_1$ of successively expanding scanned rectangular areas, will accomplish the same optical result, at perhaps a slight degradation of cosmetic appearance.

Still further, it will be understood that the radial keratotomy described in connection with FIG. 10 is illustrative of but one of a variety of keratotomy procedures to which the invention is applicable. For example, because of the great precision with which laser scan action can be microprocessor-controlled, the keratotomy may include concentric-circle loci of ablative incision, and the circular incisions may be full-circle or in a distributed pattern of circular arcs, in angularly interlaced array, as shown in FIG. 10A, the full circles or the circular arcs being with or without connected or disconnected radial incisions, as the surgeon may deem best for his particular patient's purposes. Also, as illustrated in FIG. 10B, a radial keratotomy may be implemented, again with microprocessor control of scan action with further incisions (as at 60) transverse to, and preferably not intersecting with, a particular orientation of radial incisions 61, where the radial incisions 61 are oriented to accord with the axis for which an astigmatic correction is to be made.

What is claimed is:

1. Apparatus for performing ophthalmological surgery to reduce an ascertained astigmatic condition by selective ablation of the anterior surface of the cornea with penetration into the stroma to achieve a volumetric removal of corneal tissue, said apparatus comprising laser means having a chassis and producing an output beam in the ultraviolet portion of the electromagnetic spectrum and characterized by a spot which at eye impingement is small in relation to the cornea to be operated upon, said laser means including means for adjusting beam-exposure flux to a level at which corneal-tissue ablation per unit time is to an ascertained elemental depth which is but a fraction of desired maximum depth into the stroma region, scan-deflection means positioned for deflection of said beam in a limited field about a central axis, means for steadying the cornea with respect to said chassis and with the central area of the cornea centered on the central axis of scan deflection of said beam, said scan-deflection means having X-Y coordinates of deflection for area coverage at least within the perimeter of said limited field, adjustable means for angular selection of the orientation of said coordinates to position one to the exclusion of the other of said coordinates in oriented relation to the ascertained astigmatism axis of the cornea to be operated upon, and means including a microprocessor for establishing a series of different centrally related perimeter limits of generally rectangular-area scan within the perimeter of said limited field and for coordinating the operation of said scan-deflection means in a controlled program of limitation of one area scan within one perimeter limit before repeating such coordination within the next-successive perimeter limit in the series, the successively scanned areas being of varying width and symmetrical about a central axis aligned with said astigmatism axis, whereby ablative penetration to said maximum depth is the cumulative result of plural area scans of each of a succession of different but overlapping rectangular areas, with astigmatism-reducing cornea-curvature correction.

2. Apparatus according to claim 1, and including means for effectively limiting to the perimeter of said limited field the component of scan in said one-coordinate orientation.

3. Apparatus for performing ophthalmological surgery to reduce as ascertained astigmatic condition by selective ablation of the anterior surface of the cornea with penetration into the stroma to achieve a volumetric removal of corneal tissue, said apparatus comprising laser means having a chassis and producing an output beam in the ultraviolet portion of the electromagnetic spectrum and characterized by a spot which at eye impingement is small in relation to the cornea to be operated upon, said laser means including means for adjusting beam-exposure flux to a level at which corneal-tissue ablation per unti time is to an ascertained elemental depth which is but a fraction of desired maximum depth into the stroma region, scan-deflection means positioned for deflection of said beam in a limited field about a central axis, means for steadying the cornea with respect to said chassis and with the central area of the cornea centered on the central axis of scan deflection of said beam, said scan-deflection means having two coordinates of deflection for area coverage within the perimeter of said limited field, and means including a microprocessor for coordinating the operation of said scan-deflection means in a controlled program of area coverage to establish greatest cumulative beam exposure along the alignment of the central axis of symmetry of the ascertained astigmatic condition, with cumulative beam exposure decreasing smoothly as a function of increasing lateral offset on both sides of said central axis of symmetry.

4. Apparatus for performing ophthalmological surgery to reduce an ascertained astigmatic condition by selective ablation of the anterior surface of the cornea with penetration into the stroma to achieve a volumetric removal of corneal tissue, said apparatus comprising laser means having a chassis and producing an output beam in the ultraviolet portion of the electromagnetic spectrum and characterized by a spot which at eye impingement is small, in relation to the cornea to be operated upon, said laser means including means for adjusting beam-exposure flux to a level at which corneal-tissue ablation per unit time is to an ascertained elemental depth which is but a fraction of desired maximum depth into the stroma region, scan-deflection means positioned for deflection of said beam in a limited field about a central axis, means for steadying the cornea with respect to said chassis and with the central area of the cornea centered on the central axis of scan deflection of said beam, said scan-deflection means having two coordinates of deflection for area coverage within the perimeter of said limited field, and control means for coordinating the operation of said scan-deflection means in a controlled program of area coverage to establish greatest cumulative beam exposure along the alignment of the central axis of symmetry of the ascertained astigmatic condition, with cumulative beam exposure decreasing smoothly as a function of increasing lateral offset on both sides of said central axis of symmetry.

5. Apparatus for performing ophthalmological surgery by selective ablation of the anterior surface of the cornea with varied penetration up to a predetermined maximum penetration into the stroma to achieve a cylindrical astigmatism-reducing anterior-curvature change by volumetric removal of tissue within the optically functioning area of the cornea, said apparatus comprising: a laser producing a pulsed laser beam in the ultraviolet region of the electromagnetic spectrum; means for shaping, focusing and directing the beam toward the eye with an intensity to produce tissue penetration to a depth per pulsed exposure which is but a fraction of said predetermined maximum; said means including means for selectively first determining and controlling a first rectangular area of exposure to the extent of at least said fractional depth and thereafter determining and controlling a second and different rectangular area of exposure to the extent of at least said fractional depth, each of said rectangular areas being symmetrically disposed on opposite sides of one and the same meridian of the cornea and within the optically functioning area of the cornea, wherein said meridian is selectable for orientation related to the axis of astigmatism to be reduced, and wherein the width of said rectangular area varies from one to the next rectangular area; whereby the cumulative penetration of the cornea for both said areas effects an astigmatism-correcting change in the curvature of the cornea.

6. Apparatus for perfoming ophthalmological surgery by selective ablation of the anterior surface of the cornea with varied penetration up to a predetermined maximum penetration into the stroma to achieve a cylindrical astigmatism-reducing anterior-curvature change by volumetric removal of tissue within the optically functioning area of the cornea, said apparatus comprising: a laser producing a laser beam in the ultraviolet region of the electromagnetic spectrum; means for shaping, focusing and directing the beam toward the eye with an intensity to produce tissue penetration to a depth per unit time exposure which is but a fraction of said predetermined maximum; said means including means for selectively first determining and controlling a first rectangular area of exposure to the extent of at least said fractional depth and thereafter determining and controlling a second and different rectangular area of exposure to the extent of at least said fractional depth, each said rectangular areas being symmetrically disposed on opposite sides of one and the same meridian of the cornea within the optically functioning area of the cornea, wherein said meridian is selectable for orientation related to the axis of astigmatism to be reduced, and wherein the width of said rectangular area varies from one to the next rectangular area; whereby the cumulative penetration of the cornea for both said areas effects an astigmatism-correcting change in the curvature of the cornea.

7. Apparatus for performing ophthalmological surgery to reduce an ascertained astigmatic condition by selective ablation of the anterior surface of the cornea with penetration into the stroma to achieve a volumetric removal of corneal tissue, said apparatus comprising laser means having a chassis and producing an output beam in the ultraviolet portion of the electromagnetic spectrum and characterized by a spot which at eye impingement is small in relation to the cornea to be operated upon, said laser means including means for adjusting beam-exposure flux to a level at which corneal-tissue ablation per unit time is to an ascertained elemental depth which is but a fraction of desired maximum depth into the stroma region, scan-deflection means positioned for deflection of said beam in a limited field about a central axis, means for steadying the cornea with respect to said chassis and with the central area of the cornea centered on the central axis of scan deflection of said beam, said scan-deflection means having X-Y coordinates of deflection for area coverage at least within the perimeter of said limited field, adjustable means for angular selection of the orientation of said coordinates to position one to the exclusion of the other of said coordinates in oriented relation to the ascertained astigmatism axis of the cornea to be operated upon, and control means with coordinating control connections to said scan-deflection means and to said laser for establishing a series of different centrally related perimeter limits of generally rectangular-area scan within the perimeter of said limited field and for coordinating the operation of said scan-deflection means in a controlled program of limitation of one area scan within one perimeter limit before repeating such coordination within the next-successive perimeter limit in the series, the successively scanned areas being of varying width and symmetrical about a central axis aligned with said astigmatism axis, whereby ablative penetration to said maximum depth is the cumulative result of plural area scans of each of a succession of different but overlapping rectangular areas, with astigmatism-reducing cornea-curvature correction.

8. Apparatus for performing ophthalmological surgery by selective ablation of the anterior surface of the cornea with penetration into the stroma to achieve a volumetric removal of corneal tissue, said apparatus comprising laser means having a chassis and producing an output beam in the ultraviolet portion of the electromagnetic spectrum and characterized by a spot which at cornea impingement is small in relation to the cornea to be operated upon, said laser means including means for adjusting beam-exposure flux to a level at which resultant corneal-tissue ablation per unit time is to an ascertained elemental depth which is but a fraction of the desired maximum depth of ablation into the stroma region, scan-deflection means positioned for deflection of said beam in a limited field about a central axis, means for steadying the cornea with respect to said chassis and with the central area of the cornea centered on the central axis of scan deflection of said beam, said scan-deflection means having two coordinates of deflection for area coverage within the perimeter of said central area, and means including a microprocessor for establishing a series of different centrally related perimeter limits of area-scan action within the perimeter of said central area and for coordinating the operation of said scan-deflection means in a controlled program of limitation of one area scan within one perimeter limit before repeating such coordination within the next-successive perimeter limit in the series, whereby ablative penetration to said maximum depth is the cumulative result of plural area scans of each of a succession of different but overlapping areas.

9. Apparatus according to claim 8, further comprising eye-fixation means fixed with respect to said chassis and aligned for observation through the other eye of the patient.

10. Apparatus according to claim 8, wherein said laser means is an excimer laser operative with a gas selected from the group comprising fluorine, argon fluoride, krypton fluoride, xenon chloride, and xenon fluoride.

11. Apparatus according to claim 8, wherein said laser means produces an output beam characterized by a wavelength not substantially exceeding 400 nm.

12. Apparatus according to claim 8, in which said scan-deflection means comprises mechanically displaceable optical components, and means for displacing said optical components to effect a predetermined deflection of said beam.

13. Apparatus according to claim 8, in which said laser means includes a means for reducing said beam crosssection at the eye of the patient to a spot size in the range of 30 microns to 0.5 mm.

14. Apparatus according to claim 8, in which said means for steadying the cornea includes a circumferentially continuous hollow annular ring which is air-permeable at one axial side, said side being contoured for adaptation to the corneal scleral region of an eye, and an external-connection port to the hollow of said ring for external air-evacuating connection of the same.

15. Apparatus according to claim 8, in which said scan-deflection means is radially operative with respect to the axis of said beam at incidence with the cornea, said scan-deflection means including further means for rotating the direction in which the radial deflection is operative.

16. Apparatus according to claim 15, in which said further means is continuously operative in the course of a given radial-scan operation, whereby each area scan is the result of a spirally developed course of beam deflection.

17. Apparatus according to claim 8, in which said perimeter limits are circular outer limits of successive different concentrically related scanned areas, whereby the cumulative result of microprocessor control of successive-area scanning of the cornea is myopia-correcting.

18. Apparatus according to claim 8, in which said perimeter limits are circular inner limits of successive different concentrically related scanned annular areas of constant outer diameter, whereby the cumulative result of microprocessor control of successive-area scanning of the cornea is hyperopia-correcting.

19. Apparatus according to claim 8, in which the perimeter limit of successive-area scanning is a circle of constant radius, whereby to prepare a circular corneal recess of constant depth for reception of a corneal transplant.

20. Apparatus according to claim 8, in which said microprocessor means includes means for coordinated control of said scan-deflection means in one or more adjacent concentrically related annular zonal areas and in the central circular zonal area adjacent and within the innermost annular zonal area, said innermost annular area having an outer circular perimeter which is of incrementally larger radius than that of its inner circular perimeter, and the radius of said inner circular perimeter being substantially the radius of the perimeter of said circular zonal area, said microprocessor means further including means for successive-area scanning of said innermost annular zonal area in a pattern of outer-perimeter radius variation at constant inner-perimeter radius, and for successive-area scanning of said central circular zonal area in a pattern of outer-perimeter radius variation; whereby to prepare a Fresnel-characterized myopia-correcting anterior-surface profile.

21. Apparatus according to claim 8, in which said microprocessor means includes means for coordinated control of said scan-deflection means in one or more adjacent concentrically related annular zonal areas and in the central circular zonal area adjacent and within the innermost annular zonal area, said innermost annular area having an outer circular perimeter which is of incrementally larger radius than that of its inner circular perimeter, and the radius of said inner circular perimeter being substantially the radius of the perimeter of said circular zonal area, said microprocessor means further including means for successive-area scanning of said innermost annular zonal area in a pattern of inner-perimeter radius variation at constant outer-perimeter radius, and for successive-area scanning of said central circular zonal area in a pattern of annular areas wherein the outer-perimeter radius is constant and the inner radius varies; whereby to prepare a Fresnel-characterized hyperopia-correcting anterior-surface profile.

22. Apparatus according to claim 8, in which said microprocessor means includes means for coordinated control of said scan-deflection means in each of a plurality of concentrically related contiguous annular zonal areas, the innermost of which has an inner perimeter of substantially zero inner radius, each annular zonal area having an outer circular perimeter which is of incrementally larger radius than that of its inner circular perimeter, said microprocessor means further including means for successive area scanning of each annular zonal area in a pattern of outer-perimeter radius variation at constant inner-perimeter radius; whereby to prepare a Fresnel-characterized myopia-correcting anterior-surface profile.

23. Apparatus according to claim 8, in which said microprocessor means includes means for coordinated control of said scan-deflection means in each of a plurality of concentrically related contiguous annular zonal areas, the innermost of which has an inner perimeter of substantially zero inner radius, each annular zonal area having an outer circular perimeter which is of incrementally larger radius than that of its inner circular perimeter, said microprocessor means further including means for successive area scanning of each annular zonal area in a pattern of inner-perimeter radius variation at constant outer-perimeter radius; whereby to prepare a Fresnel-characterized hyperopia-correcting anterior-surface profile.

24. Apparatus for performing ophthalmological surgery by selective ablation of the anterior surface of the cornea with penetration into the stroma to achieve a volumetric removal of corneal tissue, said apparatus comprising laser means having a chassis and producing an output beam in the ultraviolet portion of the electromagnetic spectrum and characterized by a relatively small spot at cornea impingement, said laser including means for adjusting beam-exposure flux to a level at which resultant corneal-tissue ablation per unit time is to an ascertained elemental depth which is but a fraction of desired maximum depth of ablation into the stroma region of the cornea, scan-deflection means positioned for deflection of said beam in a limited field about a central axis, means for steadying the cornea with respect to said chassis and with the central area of the cornea centered on the central axis of scan deflection of said beam, said scan-deflection means having two coordinates of deflection for area coverage within the perimeter of said central area, and means including a microprocessor for coordinating the operation of said scan-deflection means in a controlled program of concentric-circle coverage to establish greatest cumulative beam exposure of a least-radius circular area and least cumulative beam exposure of a greatest-radius circular area, whereby to effect a myopia-correcting curvature change in the external surface of the cornea.

25. Apparatus for performing ophthalmological surgery by selective ablation of the anterior surface of the cornea with penetration into the stroma to achieve a volumetric removal of corneal tissue, said apparatus comprising laser means having a chassis and producing an output beam in the ultraviolet portion of the electromagnetic spectrum and characterized by a relatively small spot at cornea impingement, said laser including means for adjusting beam-exposure flux to a level at which resultant corneal-tissue ablation per unit time is to an ascertained elemental depth which is but a fraction of desired maximum depth of ablation into the stroma region of the cornea, scan-deflection means positioned for deflection of said beam in a limited field about a central axis, means for steadying the cornea with respect to said chassis and with the central area of the cornea centered on the central axis of scan deflection of said beam, said scan-deflection means having two coordinates of deflection for area coverage within the perimeter of said central area, and means including a microprocessor for coordinating the operation of said scan-deflection means in a controlled program of concentric-circle coverage to establish greatest cumulative beam exposure of a greatest-radius circular area and least cumulative beam exposure of a least-radius circular area, whereby to effect a hyperopia-correcting curvature change in the external surface of the cornea.

26. Apparatus for performing ophthalmological surgery by selective ablation of the anterior surface of the cornea with penetration into the stroma to achieve a volumetric removal of corneal tissue, said apparatus comprising laser means producing an output beam in the ultraviolet portion of the electromagnetic spectrum and characterized by a spot which at cornea impingement is small in relation to the cornea to be operated upon, said laser means including means for adjusting beam-exposure flux to a level at which resultant corneal-tissue ablation per unit time is to an ascertained elemental depth which is but a fraction of a predetermined maximum depth of ablation into the stroma, scan-deflection means positioned for deflection of said beam in a limited field about a central axis, said scan-deflection means having two coordinates of deflection for area coverage within the perimeter of said limited field, and control means with coordinating control connections to said scan-deflection means and to said laser for varying the perimeter of successive area scans within said field wherein said area scans are symmetrical about the central axis, whereby said scan-deflection means may perform one area scan within one perimeter limit before performing another area scan within another perimeter limit, whereby to effect a controlled sculpturing action upon the cornea to alter the optical properties thereof.

27. Apparatus for performing ophthalmological surgery by selective ablation of the anterior surface of the cornea with penetration into the stroma to achieve a volumetric removal of corneal tissue, said apparatus comprising laser means producing an output beam in the ultraviolet portion of the electromagnetic spectrum and characterized by a spot which at cornea impingement is small in relation to the cornea to be operated upon, said laser means including means for adjusting beam-exposure flux to a level at which resultant corneal-tissue ablation per unit time is to an ascertained elemental depth which is but a fraction of a predetermined maximum depth of ablation into the stroma, scan-deflection means positioned for deflection of said beam in a limited circular field of maximum radius about a central axis, said scan-deflection means having two coordinates of deflection for area coverage within the circumference of said circular field, and control means with coordinating control connections to said scan-deflection means and to said laser for varying the radius from one to another area scan within said circular field, whereby successive area scans may be circular and at different radii about the central axis, whereby to effect a controlled sculpturing action upon the cornea to effect a myopia-reducing alteration of the optical properties thereof.

28. Apparatus for performing ophthalmological surgery by selective ablation of the anterior surface of the cornea with penetration into the stroma to achieve a volumetric removal of corneal tissue, said apparatus comprising laser means producing an output beam in the ultraviolet portion of the electromagnetic spectrum and characterized by a spot which at cornea impingement is small in relation to the cornea to be operated upon, said laser means including means for adjusting beam-exposure flux to a level at which resultant corneal-tissue ablation per unit time is to an ascertained elemental depth which is but a fraction of a predetermined maximum depth of ablation into the stroma, scan-deflection means positioned for deflection of said beam in a limited circular field of maximum radius about a central axis, said scan-deflection means having two coordinates of deflection for area coverage within the circumference of said circular field, and control means with control connections to said scan-deflection means and to said laser for varying between a minimum and substantially said maximum the inner radius of an annular area having its outer radius at said maximum, said inner radius variation being from one to another annular-area scan, whereby successive area scans may be annular and with different inner radii about the central axis, whereby to effect a controlled sculpturing action upon the cornea to effect a hyperopia-reducing alteration of the optical properties thereof.

29. Apparatus for performing ophthalmological surgery by selective ablation of the anterior surface of the cornea with penetration into the stroma to achieve a volumetric removal of corneal tissue, said apparatus comprising laser means producing an output beam in the ultraviolet portion of the electromagnetic spectrum and characterized by a spot which at cornea impingement is small in relation to the cornea to be operated upon, said laser means including means for adjusting beam-exposure flux to a level at which resultant corneal-tissue ablation per unit time is to an ascertained elemental depth which is but a fraction of a predetermined maximum depth of ablation into the stroma, scan-deflection means positioned for deflection of said beam in a limited field about a central axis, said scan-deflection means having two coordinates of deflection for area coverage within the perimeter of said limited field, and control means coordinating control connections to said scan-deflection means and to said laser for determining a succession of area scans of said field, whereby said scan-deflection means may perform one area scan within said perimeter limit before performing another area scan within said perimeter limit, whereby to effect an ablative excavation of predetermined substantially uniform depth into the stroma.

30. Apparatus for performing ophthalmological surgery by selective ablation of the anterior surface of the cornea with varied penetration up to a predetermined maximum penetration into the stroma to achieve an anterior-curvature change by volumetric removal of tissue within the optically functioning area of the cornea, said apparatus comprising: a laser producing a pulsed laser beam in the ultraviolet region of the electromagnetic spectrum; means for shaping, focusing and directing the beam toward the cornea with an intensity to produce tissue penetration to a depth per pulsed exposure which is but a fraction of said predetermined maximum; said means including means for selectively (a) determining and controlling one circular area of exposure to the extent of at least said fractional depth and (b) determining and controlling a different circular area of exposure to the extent of at least said fractional depth, each of said circular areas being within the optically functioning area of the cornea and concentrically disposed with respect to the optical axis of the cornea; whereby the cumulative penetration of the cornea for both said areas of exposure can effect a myopia-reducing corrective change in the curvature of the cornea.

31. Apparatus for performing ophthalmological surgery by selective ablation of the anterior surface of the cornea with varied penetration up to a predetermined maximum penetration into the stroma to achieve an anterior-curvature change by volumetric removal of tissue within the optically functioning area of the cornea, said apparatus comprising: a laser producing a laser beam in the ultraviolet region of the electromagnetic spectrum; means for shaping, focusing and directing the beam toward the cornea with an intensity to produce tissue penetration to a depth per unit time exposure which is but a fraction of said predetermined maximum; said means including means for selectively (a) determining and controlling one circular area of exposure to the extent of at least said fractional depth and (b) determining and controlling a different circular area of exposure to the extent of at least said fractional depth, each of said circular areas being within the optically functioning area of the cornea and concentrically disposed with respect to the optical axis of the cornea; whereby the cumulative penetration of the cornea for both said areas of exposure can effect a myopia-reducing corrective change in the curvature of the cornea.

32. Apparatus for performing ophthalmological surgery by selective ablation of the anterior surface of the cornea with varied penetration up to a predetermined maximum penetration into the stroma to achieve an anterior-curvature change by volumetric removal of tissue within the optically functioning area of the cornea, said apparatus comprising: a laser producing a pulsed laser beam in the ultraviolet region of the electromagnetic spectrum; means for shaping, focusing and directing the beam toward the cornea with an intensity to produce tissue penetration to a depth per pulsed exposure which is but a fraction of said predetermined maximum; said means including means for selectively (a) determining and controlling one circularly annular area of exposure to the extent of at least said fractional depth and (b) determining and controlling a different circularly annular area of exposure to the extent of at least said fractional depth, each of said circularly annular areas being within the optically functioning circular area of the cornea and concentrically disposed with respect to the optical axis of the cornea; said areas having overlapping relation at least to the outer diameter of the optically functioning area, and one of said annular areas having a lesser inner diameter than the other of said annular areas; whereby the cumulative penetration of the cornea for both said annular areas of exposure can effect a hyperopia-reducing corrective change in the curvature of the cornea.

33. Apparatus for performing ophthalmological surgery by selective ablation of the anterior surface of the cornea with varied penetration up to a predetermined maximum penetration into the stroma to achieve an anterior-curvature change by volumetric removal of tissue within the optically functioning area of the cornea, said apparatus comprising: a laser producing a laser beam in the ultraviolet region of the electromagnetic specturm; means for shaping, focusing and directing the beam toward the cornea with an intensity to produce tissue penetration to a depth per unit time exposure which is but a fraction of said predetermined maximum; said means including means for selectively (a) determining and controlling one circularly annular area of exposure to the extent of at least said fractional depth and (b) determining and controlling a different circularly annular area of exposure to the extent of at least said fractional depth, each of said circularly annular areas being within the optically functioning circular area of the cornea and concentrically disposed with respect to the optical axis of the cornea, said areas having overlapping relation at least to the outer diameter of the optically functioning area, and one of said annular areas having a lesser inner diameter than the other of said annular areas; whereby the cumulative penetration of the cornea for both said areas can effect a hyperopia-reducing corrective change in the curvature of the cornea.

34. Apparatus for performing ophthalmological surgery by selective ablation of the anterior surface of the cornea with varied penetration up to a predetermined maximum penetration into the stroma to achieve an anterior-curvature change by volumetric removal of tissue within the optically functioning area of the cornea, said apparatus comprising: a laser producing a pulsed laser beam in the ultraviolet region of the electromagnetic spectrum; means for shaping, focusing and directing the beam toward the cornea with an intensity to produce tissue penetration to a depth per pulsed exposure which is but a fraction of said predetermined maximum; said means including control means for selectively determining and controlling one corneal area of laser-beam exposure to the extent of at least said fractional depth (a) in one or more adjacent concentrically related annular zones within the optically functioning area of the cornea and (b) in the central circular zonal area adjacent and within the innermost annular zonal area, said innermost annular area having an outer circular perimeter which is of incrementally larger radius than that of its inner circular perimeter, and the radius of said inner circular perimeter being substantially the radius of the perimeter of said circular zonal area; said control means further selectively determining and controlling other corneal areas of laser-beam exposure to the extent of at least said fractional depth wherein for the innermost annular zonal area the outer-perimeter radius varies and the inner-perimeter radius is constant, and wherein for the central circular zonal area the outer-perimeter radius varies; whereby the cumulative corneal penetration of the cornea for both said corneal-area exposures can effect a Fresnel-characterized myopia-reducing corrective change in the curvature of the cornea.

35. Apparatus for performing ophthalmological surgery by selective ablation of the anterior surface of the cornea with varied penetration up to a predetermined maximum penetration into the stroma to achieve an anterior-curvature change by volumetric removal of tissue within the optically functioning area of the cornea, said apparatus comprising: a laser producing a laser beam in the ultraviolet region of the electromagnetic spectrum; means for shaping, focusing and directing the beam toward the cornea with an intensity to produce tissue penetration to a depth per unit time exposure which is but a fraction of said predetermined maximum; said means including control means for selectively determining and controlling one corneal area of laser-beam exposure to the extent of at least said fractional depth (a) in one or more adjacent concentrically related annular zones within the optically functioning area of the cornea and (b) in the central circular zonal area adjacent and within the innermost annular zonal area, said innermost annular area having an outer circular perimeter which is of incrementally larger radius than that of its inner circular perimeter, and the radius of said inner circular perimeter being substantially the radius of the perimeter of said circular zonal area; said control means further selectively determining and controlling other corneal areas of laser-beam exposure to the extent of at least said fractional depth wherein for the innermost annular zonal area the outer-perimeter radius varies and the inner-perimeter radius is constant, and wherein for the central circular zonal area the outer-perimeter radius varies; whereby the cumulative corneal penetration of the cornea for both said corneal-area exposures can effect a Fresnel-characterized myopia-reducing corrective change in the curvature of the cornea.

36. Apparatus for performing ophthalmological surgery by selective ablation of the anterior surface of the cornea with varied penetration up to a predetermined maximum penetration into the stroma to achieve an anterior-curvature change by volumetric removal of tissue within the optically functioning area of the cornea, said apparatus comprising: a laser producing a pulsed laser beam in the ultraviolet region of the electromagnetic spectrum; means for shaping, focusing and directing the beam toward the cornea with an intensity to produce tissue penetration to a depth per pulsed exposure which is but a fraction of said predetermined maximum; said means including control means for selectively determining and controlling one corneal area of laser-beam exposure to the extent of at least said fractional depth (a) in one or more adjacent concentrically related annular zones within the optically functioning area of the cornea and (b) in the central circular zonal area adjacent and within the innermost annular zonal area, said innermost annular area having an outer circular perimeter which is of incrementally larger radius than that of its inner circular perimeter, and the radius of said inner circular perimeter being substantially the radius of the perimeter of said circular zonal area; said control means further selectively determining and controlling other corneal areas of laser-beam exposure to the extent of at least said fractional depth wherein for the innermost annular zonal area the outer-perimeter radius is constant and the inner-perimeter radius varies, and wherein for the central circular zonal area the outer-perimeter radius is constant and the inner-perimeter radius varies; whereby the cumulative corneal penetration of the cornea for both said cornea-area exposures can effect a Fresnel-characterized hyperopia-reducing corrective change in the curvature of the cornea.

37. Apparatus for performing ophthalmological surgery by selective ablation of the anterior surface of the cornea with varied penetration up to a predetermined maximum penetration into the stroma to achieve an anterior-curvature change by volumetric removal of tissue within the optically functioning area of the cornea, said apparatus comprising: a laser producing a laser beam in the ultraviolet region of the electromagnetic spectrum; means for shaping, focusing and directing the beam toward the cornea with an intensity to produce tissue penetration to a depth per unit time exposure which is but a fraction of said predetermined maximum; said means including control means for selectively determining and controlling one corneal area of laser-beam exposure to the extent of at least said fractional depth (a) in one or more adjacent concentrically related annular zones within the optically functioning area of the cornea and (b) in the central circular zonal area adjacent and within the innermost annular zonal area, said innermost annular area having an outer circular perimeter which is of incrementally larger radius than that of its inner circular perimeter, and the radius of said inner circular perimeter being substantially the radius of the perimeter of said circular zonal area; said control means further selectively determining and controlling other corneal areas of laser-beam exposure to the extent of at least said fractional depth wherein for the innermost annular zonal area the outer-perimeter radius is constant and the inner-perimeter radius varies, and wherein for the central circular zonal area the outer-perimeter radius is constant and the inner-perimeter radius varies; whereby the cumulative corneal penetration of the cornea for both said cornea-area exposures can effect a Fresnel-characterized hyperopia-reducing corrective change in the curvature of the cornea.

38. Apparatus for performing ophthalmological surgery by selective ablation of the anterior surface of the cornea with varied penetration up to a predetermined maximum penetration into the stroma to achieve an anterior-curvature change by volumetric removal of tissue within the optically functioning area of the cornea, said apparatus comprising: a laser producing a pulsed laser beam in the ultraviolet region of the electromagnetic spectrum; means for shaping, focusing and directing the beam toward the cornea with an intensity to produce tissue penetration to a depth per pulsed exposure which is but a fraction of said predetermined maximum; said means including means for selectively determining and controlling a circular area of exposure to the extent of at least said fractional depth and thereafter determining and controlling one or more further like and coaxially related circular areas of exposure to the extent of at least said fractional depth, each of said areas including the optically functioning area of the cornea; whereby the cumulative penetration of the cornea for said corneal-area exposures will prepare a circular corneal recess of constant depth for reception of a corneal transplant.

39. Apparatus for performing ophthalmological surgery by selective ablation of the anterior surface of the cornea with varied penetration up to a predetermined maximum penetration into the stroma to achieve an anterior-curvature change by volumetric removal of tissue within the optically functioning area of the cornea, said apparatus comprising: a laser producing a laser beam in the ultraviolet region of the electromagnetic spectrum; means for shaping, focusing and directing the beam toward the cornea with an intensity to produce tissue penetration to a depth per unit time exposure which is but a fraction of said predetermined maximum; said means including means for selectively determining and controlling a circular area of exposure to the extent of at least said fractional depth and thereafter determining and controlling one or more further like and coaxially related circular areas of exposure to the extent of at least said fractional depth, each of said areas including the optically functioning area of the cornea; whereby the cumulative penetration of the cornea for said corneal-area exposures will prepare a circular corneal recess of constant depth for reception of a corneal transplant.

40. Apparatus for performing ophthalmological surgery to reduce an ascertained astigmatic condition by selective ablation of the anterior surface of the cornea with varied penetration up to a predetermined maximum penetration into the stroma to achieve an anterior-curvature change by volumetric removal of tissue within the optically functioning area of the cornea, said apparatus comprising: a laser producing a pulsed laser beam in the ultraviolet region of the electromagnetic spectrum; means for shaping, focusing and directing the beam toward the cornea with an intensity to produce tissue penetration to a depth per pulsed exposure which is but a fraction of said predetermined maximum; said means including means for selectively (a) determining and controlling one rectangular area of exposure to the extent of at least said fractional depth and (b) determining and controlling a different rectangular area of exposure to the extent of at least said fractional depth, said rectangular areas being of varying width and symmetrical about a central axis through the optical axis of the cornea and oriented in accordance with the ascertained astigmatic condition; whereby the cumulative penetration of the cornea for both said areas of exposure can effect an astigmatism-reducing corrective change in the curvature of the cornea.

41. Apparatus for performing ophthalmological surgery to reduce an ascertained astigmatic condition by selective ablation of the anterior surface of the cornea with varied penetration up to a predetermined maximum penetration into the stroma to achieve an anterior-curvature change by volumetric removal of tissue within the optically functioning area of the cornea, said apparatus comprising: a laser producing a laser beam in the ultraviolet region of the electromagnetic spectrum; means for shaping, focusing and directing the beam toward the cornea with an intensity to produce tissue penetration to a depth per unit time exposure which is but a fraction of said predetermined maximum; said means including means for selectively (a) determining and controlling one rectangular area of exposure to the extent of at least said fractional depth and (b) determining and controlling a different rectangular area of exposure to the extent of at least said fractional depth, said rectangular areas being of varying width and symmetrical about a central axis through the optical axis of the cornea and oriented in accordance with the ascertained astigmatic condition; whereby the cumulative penetration of the cornea for both said areas of exposure can effect an astigmatism-reducing corrective change in the curvature of the cornea.

* * * * *